United States Patent [19]

Davy et al.

[11] Patent Number: 5,679,710
[45] Date of Patent: Oct. 21, 1997

[54] HIGH REFRACTIVE INDEX AND/OR RADIO-OPAQUE RESINS SYSTEMS

[75] Inventors: Kenneth Walter Michael Davy, Midhurst; Roberto Labella, London, both of United Kingdom

[73] Assignee: London Hospital Medical College, London, United Kingdom

[21] Appl. No.: 548,406

[22] Filed: Oct. 26, 1995

Related U.S. Application Data

[63] Continuation-in-part of Ser. No. 447,237, May 22, 1995, abandoned.

[30] Foreign Application Priority Data

Nov. 1, 1994 [GB] United Kingdom ............ 9422008

[51] Int. Cl.$^6$ ............ A61K 31/215; A61K 31/225; A61K 6/08; A61C 5/00
[52] U.S. Cl. ............ 514/547; 514/549; 433/222.1; 433/228.1
[58] Field of Search ............ 514/547, 549; 433/222.1, 228.1

[56] References Cited

U.S. PATENT DOCUMENTS

| | | | |
|---|---|---|---|
| 3,346,620 | 10/1967 | Siggins et al. | 260/476 |
| 5,055,497 | 10/1991 | Okada et al. | 523/116 |

FOREIGN PATENT DOCUMENTS

| | | |
|---|---|---|
| 40987/85 | 3/1988 | Australia . |
| 268157 | 5/1988 | European Pat. Off. . |
| 401385 | 12/1990 | European Pat. Off. . |
| 2647890 | 5/1977 | Germany . |
| 3342601 | 3/1985 | Germany . |
| 1526888 | 9/1978 | United Kingdom . |

OTHER PUBLICATIONS

Espelid et al., "Radiopacity of Restoration and Detection of Secondary Caries." Dental Mater. 7:114–117 (1991).

Ferracane et al., "Fourier Transform Infrared Analysis of Degree of Polymerization in Unfilled Resins—Methods Comparison." J. Dent. Res. 63(8):1093–1095 (1984).

Ruyter et al., "Conversion in Different Depths of Ultraviolet and Visible Light Activated Composite Materials." Acta. Odontol. Scand. 40:179–192 (1982).

Soderholm, "Degradation of Glass Filler in Experimental Composites." J. Dent. Res. 60:1867–1875 (1981).

Soderholm, "Filler Leachability During Water Storage of Six Composite Materials." J. Dent. Res. 98:82–88 (1990).

*Primary Examiner*—Phyllis G. Spivack
*Attorney, Agent, or Firm*—Fitch, Even, Tabin & Flannery

[57] ABSTRACT

A dental composition is disclosed which comprises a resin base comprising at least one brominated or iodinated acrylate or methacrylate monomer having a high refractive index of above 1.6, in admixture with a filler material which has a refractive index of ±0.05 of the refractive index of the said resin base.

The filler material is radio-opaque and is apatite, hydroxyapatite, a modified hydroxyapatite, wollastonite or a powdered cross-linked polymer.

14 Claims, No Drawings

HIGH REFRACTIVE INDEX AND/OR RADIO-OPAQUE RESINS SYSTEMS

This application is a continuation-in-part of Ser. No. 08/447,237, filed May 22, 1995, abandoned.

The present invention relates to high refractive index and/or radio-opaque resin systems and, in particular, to the development of such systems for dental applications.

A good translucency to visible light and an appropriate X-ray opacity are two major requirements for modern dental resins and dental resin composites.

The aesthetic value of a resin based restorative material is often judged on the ability of the material to match the optical properties of dental enamel and dentine, which it is designed to substitute. This is particularly desirable so that the dental restoration will have a life-like lustre appearance. Furthermore in the case of partial reconstructions, the restorative material is expected to blend with the surrounding sound tooth structure so that the contour of the restoration is not recognizable to the observer.

Visible light photoinitiation is commonly used for the polymerization of one-part resin based systems largely employed in restorative dentistry. The dental practitioner prefers light-cured materials to chemically activated materials which employ two-part systems and which require a mixing procedure. Light-cure systems are not subjected to dosage errors and entrapment of air and, above all, offer prolonged working times. However light-cured systems present the disadvantage of requiring optimal transmission of the activating light throughout the material. Reduced translucency to the activating light normally results in a shallow depth of cure, with those parts of the material more distant from the light source reacting to a lesser extent. The deleterious nature of unpolymerized resin is a major concern for the longevity of the materials. The mechanical properties, water absorption properties, wear resistance and colour stability can all be affected negatively by the presence of a large fraction of unsaturated reactive groups.

An important requirement for dental restorative materials is for the materials to appear on standard dental X-ray films as radio-opaque substances, as distinct from the surrounding tooth. The presence of immediate postoperative defects or the development of secondary caries in the surrounding tooth can only be detected when the restorative material is more radio-opaque than dental enamel. More recently the general consensus tends to be that the ideal material should be only slightly more radio-opaque than dental enamel.

In many dental applications the longevity of resin based materials has been dramatically improved by the addition of reinforcing inorganic fillers in a particulate form. If the filler particles are also radio-opaque the problem of the lack of radio-opacity of the restorative materials can also be addressed. However, the radio-opacity and visual translucency requirements of the dental restorative materials are often in conflict. One approach has been to add to the oxides of radio-opacifying elements, such as Ba, Zn, Sr and Zr, to silica glass fillers. The refractive index of these oxides is high and thus the ratio of silica to the metal oxide has to be studied carefully in order that the desired degree of radio-opacity coincides with the desired refractive index, that is a refractive index which matches that of the resin matrix. The matching is usually achieved by carefully making the particles entirely amorphous or by reducing their over-all scattering coefficient using lower volume fractions and/or lower average particle size. Another approach has been the use of metal oxides known not only for their intense radio-opacity but also their visual-opacifying power (e.g. $ZrO_2$) when interspersed in a silicate glass media. However the visual opacity of the filler is kept low by keeping the diameter of the crystalline microregions well below 0.35 micrometers, that is below the wave length of visible light.

Another limitation is that the choice of possible fillers is restricted to those which approach the refractive index of the currently available resin systems, that is approximately between 1.45 to 1.55. Assuming a maximum mismatch tolerance of 0.05, then all of those inorganic fillers with a refractive index higher than 1.60 are automatically excluded from being taken in consideration as possible candidates. The refractive index of dental enamel is about 1.65 and thus with the current systems matching of the dental restorative materials to dental enamel cannot be achieved.

There is also a heed for a class of filler which is hydrolytically more stable than the most commonly used Ba and Sr silicate glasses from which Ba, Sr and Si ions leach out in an aqueous environment. The slow degradation of the filler surface causes debonding from the resin matrix. Concern has also been expressed over the toxicity of Ba ions.

In our copending U.S. patent application No. 08/447237 we have described certain (meth)acrylate monomers which exhibit X-ray opacity and which can be incorporated into denture base compositions based on polymethacrylate. These monomers have the general formula:

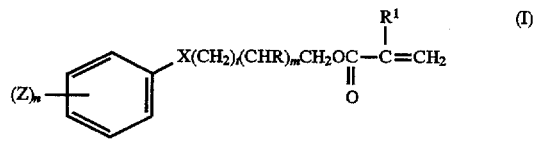

where X is —O—

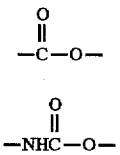

R is H, OH, $CH_3$,

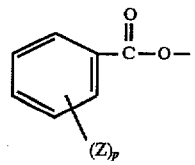

methacryloyloxy or acryloyloxy, $R^1$ is H or $CH_3$

Z is Br or I, or a mixture of these substituents m is 0 or 1 n is 3 to 5 p is 3 to 5 and t is 0 or 1, with the proviso that when X is O then R is OH

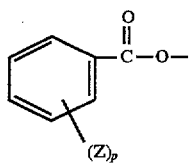

or methacryloyloxy or acryloyloxy and m is 1.

The materials as described in this earlier application which are substituted with a plurality of iodo groups on the phenyl ring also exhibit high refractive indices.

We have now appreciated that high refractive index resins which match the refractive index of the radio-opaque filler would render the above-identified complicated tailoring of filler microstructure unnecessary. Furthermore, high refractive index resins which are also radio-opaque are capable of providing part or all of the radio-opacity of the composite resin. Furthermore, certain radio-opaque/ high refractive index materials, such as apatites, may be used as filler materials with the high refractive index resins.

Accordingly, the present invention provides a dental composition which comprises a resin base comprising at least one brominated or iodinated acrylate or methacrylate monomer having a high refractive index of above 1.6, in admixture with a filler material which has a refractive index of plus or minus 0.05 of the refractive index of the said resin base.

Generally, acrylate and methacrylate monomers which include within their structures one or more tri-iodophenyl or tri-iodobenzoyl substituents, such as 2,4,6-triido-phenyl or 2,3,5-triiodobenzoyl substituents will exhibit a high refractive index. For example, the iodinated acrylate or methacrylate monomer having a high refractive index of above 1.6 may be a monomer having the general formula (I) as defined above where Z is Br or I.

Examples of monomers which have a high refractive index of above 1.6 are 2-(2,3,5-triiodobenzoyloxy)propyl methacrylate, 2-hydroxy-3-(2,4,6-triiodophenoxy) propylmethacrylate and 2-hydroxy-3-(2,3,5-triiodobenzoyloxy)propylmethacrylate.

Other monomers which possess high refractive indices include brominated or iodinated aromatic esters of bisglycidyl(meth)acrylate of the general formula:

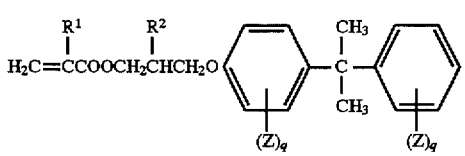

Z=Br or I, or a mixture of these substituents

P=3 to 5

R$^1$=H or CH$_3$ q=2 to 4 in each ring.

An example of a monomer of Formula II which has the desired high refractive index is 2,2(bis-[2-(2,3,5-triiodobenzoyloxy) 3-methacryloyloxypropoxy]-phenyl)propane.

Or other dimethacrylate esters given by the general formula:

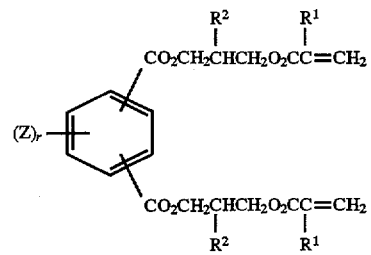

where R$^2$=H, OH or

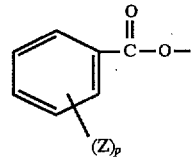

Z=Br or I, or a mixture of these substituents
p=3 to 5
R$^1$=H or CH
r=1 to 4.

It will be understood that the acrylate or methacrylate monomers of the present invention may contain an asymmetric carbon atom and it is intended that the different isomers of the monomers are included with the scope of the present invention, as well as the racemic mixtures thereof.

The incorporation into the dental compositions of the present invention of the high refractive index acrylate or methacrylate monomer enables compositions with refractive indexes tailored to the specific filler of choice to be prepared. For example, the resin base of the composition may itself have a high refractive index of above 1.6, making it suitable for use with fillers which have high refractive indices of 1.6 or above. Non-limiting examples of fillers with refractive indices of above 1.6 are high refractive index silica glass fillers, calcium silicate based fillers such as wollastonite and calcium-phosphate fillers such as apatites, hydroxyapatites or modified hydroxyapatite compositions.

Alternatively, the high refractive index acrylate or methacrylate monomer may be mixed with one or more other acrylate or methacrylate monomers or polymers having a refractive index of below 1.6, thus reducing the refractive index of the resin base to below 1.6. Filler materials with an appropriate refractive index to match the refractive index of the resin base can then be selected for use in the compositions of the present invention. Examples of other materials for use are well known to those skilled in the art, such as silicate glasses with or without the addition of X-ray opacifying agents, silica in vitreous form or as crystalline quartz, calcium phosphate fillers, or polymerized organic materials. The filler material may be treated with a coupling agent which is capable of reacting with the filler particles and the polymerizable monomer with the effect of increasing the strength of the bond between the filler and the cured polymer matrix. Examples of suitable coupling agents include

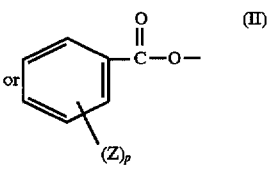

silanes, e.g. γ-methacryloxypropyl-trimethoxysilane, γ-aminopropyltriethoxysilane and γ-glycidoxypropyltrimethoxysilane.

It is also advantageous if the filler materials are radio-opaque since they can then be used in dental restorative materials where the filler materials will appear on standard dental X-ray films as radio-opaque substances. The filler material used in the invention will generally have an average particle size in the range of from 0.5 to 50 μm.

The resin base of the dental compositions of the present invention may comprise, in addition to the high refractive index acrylate or methacrylate monomer, one or more other acrylate or methacrylate monomers or polymers. Examples of suitable monomers are 2,2-(bis[3-methacryloyloxypropoxy]phenyl)propane (bis-GMA), or low viscosity analogues thereof, a urethane dimethacrylate, tetraethylene glycol dimethacrylate, triethylene glycol dimethacrylate, or tetrahydro furfuryl methacrylate. Examples of suitable polymers are those prepared from the monomers detailed above ground to a fine powder.

The resin base of the dental compositions of the present invention will generally include a light, heat or self curing system which may comprise a free radical catalyst, such as a peroxide or a peroxide/ amine initiator system, a photo-initiator system, such as camphor quinone/tertiary amine, or a combination thereof.

The dental compositions of the present invention may also include other additives such as inhibitors, pigments, dyes and/or other ingredients well known to those skilled in the art.

The matching of the refractive index of the filler material used in the dental composition of the present invention to within plus or minus 0.05, preferably plus or minus 0.005 of the refractive index of the base resin is an extremely important feature of the invention.

One further advantage of the acrylate or methacrylate monomers used in the present invention derives from their high molecular weight, as polymerization shrinkage is inversely related to the molecular weight of the monomer. Accordingly, the observed shrinkage on polymerisation of formulations containing these high molecular weight iodine or bromine monomers will be less than observed with monomer formulations that do not include such high molecular weight monomers.

It will be understood that the monomers used in the present invention may be solid or liquid and the use of either liquid or solid monomers falls within the scope of the present invention.

One particular advantage of the acrylate or methacrylate momomers used in the present invention is the presence of bromide or iodine which confers X-ray opacity and this property maybe used to enhance the X-ray opacity of the derived composite and hence allow less X-ray opaque fillers to be used in the composite formulation.

A further application of the iodinated acrylate and methacrylate monomers of the present invention concerns the use of high refractive index polymeric glasses as fillers. The monomers polymerize to thermally stable glasses possessing high refractive indices and intense X-ray opacity. Such homopolymers or copolymers with dimethacrylate such as bisglycidyl-methacrylate or urethane dimethacrylate would be suitable as polymeric glass fillers for the monomers described in the present invention.

It will be understood that the acrylate or methacrylate monomers of the present invention may contain an asymmetric carbon atom and it is intended that the different isomers of the monomers are included within the scope of the present invention, as well as racemic mixtures thereof.

The present invention will be further described with reference to the following non-limiting Examples.

EXAMPLE 1

2,2(Bis-[2-(2,3,5-triiodobenzoloxy)3-methacryloxyloxypropoxy)phenyl)propane

A solution of 2,3,5-triiodobenzoyl chloride (50.0 g) in dichloromethane (200 ml) was added slowly over a period of 30 minutes to a cold solution of pyridine (8.0 g) in dichloromethane (200 ml) placed in a three-necked flask immersed in an ice water bath equipped with mechanical stirrer, a reflux condenser with the exit protected by a calcium chloride guard tube, a thermometer and a pressure equalizing dropping funnel maintaining the temperature below 10° C. When all of the acid chloride had been added a solution of bis-GMA (20.0 g) in dichloromethane (100 ml) was added slowly over a period of three hours whilst maintaining the temperature of the stirred solution below 10° C. Finally the mixture was allowed to stir overnight at room temperature.

The contents of the flask were filtered and the organic phase extracted repeatedly with dilute hydrochloric acid and then repeatedly with a saturated solution of sodium bicarbonate. The organic phase was dried (sodium sulphate) and the solvent removed under reduced pressure to give 36 g of a pale brown semi-crystalline material 2,2(bis-[2-(2,3,5-triiodo-benzoyloxy)3-methacryloyloxypropoxy)phenyl)propane.

Calc.for $C_{43}H_{38}O_{10}I_6$: C 34.85% found C 34.68%

H 2.56% found H 2.68%

The refractive index of the title compound was 1.649.

EXAMPLE 2

Preparation of 2-(2,3,5-triiodobenzoxy)propylmethacrylate

A solution of 2,3,5-triiodobenzoyl chloride (100 g) in dichloromethane (450 ml) was added over a period of three hours to a cold (5° C.) stirred solution of 2-hydropropyl methacrylate (29.0 g) and pyridine (16.0 g) in dichloromethane (350 ml) whilst maintaining the temperature of the mixture 5°–10° C. After all the acid chloride had been added the mixture was stirred overnight at room temperature. The solid was filtered off, washed with fresh dichloromethane and the combined dichloromethane solution was extracted with dilute HCl (6×100 ml, 0.2M) and then with saturated sodium bicarbonate solution. The organic phase was dried ($MgSO_4$) and the solvent removed under reduced pressure to give 97.2 g of a brown oil which crystallised on standing. Three recrystallisations from ether gave a pure material as a white crystalline solid m. pt 70° C. (DSC).

Calc. for $C_{14}H_{13}O_4I_3$: C 26.87% found C 26.98%

H 2.08% found H 2.17%

The refractive index of the crude oil from the reaction mixture was 1.610.

EXAMPLE 3

2-Hydroxy-3-(2,4,6-triodophenoxy)propylmethacrylate 0.1 mol of 2,4,6-tri-iodophenol was stirred with 0.1 mol of glycidyl methacrylate at 65° C. in the presence of 1 to 2% hydroquinone polymerisation inhibitor and 1 to 2% of N,N'-dimethyl-p-toluidine. After 18 hours the liquid was dissolved in ethyl acetate and extracted repeatedly with dilute HCl (0.2M) and then with saturated sodium bicarbonate solution. The organic phase was removed under reduced pressure and the resulting crystalline solid recrystallised three times from diethyl ether to give as a white solid, 2-hydroxy-3-(2,4,6-triodophenoxy)-propylmethacrylate m.pt. 92° C.; yield (90%).

calc. for $C_{13}H_{13}O_4I_3$: C 26.12% found C 26.05%
H 2.17% found H 2.20%

EXAMPLE 4

2-Hydroxy-3-(2,3,5-triiodobenzoyloxy) propylmethacrylate 100 g (0.2 mol) of 2,3,5-triiodobenzoic acid was stirred with 28.4 g of glycidyl methacrylate at 48°–50° C. in the presence of 4% w/w triethylamine. After 5 hours the resulting liquid was dissolved in methyl acetate (200 ml) and extracted repeatedly with dilute HCl (2.0M) and then with saturated sodium bicarbonate solution. The organic phase was dried (MgSO$_4$) and the solvent was removed under reduced pressure and the resulting yellow oil was passed through a short dry column of silica gel and charcoal to give 2-hydroxy-3-(2,3,5-triiodobenzoyloxy)propylmethacrylate as an almost colourless oil (yield 42.2 g).

Calc. for $C_{14}H_{13}O_5I_3$: C 26.20% H=2.03%
found C 26.24% H=2.55%

The refractive index of the monomer was 1.631.

EXAMPLE 5

Preparation of 2,3-dimethacryloxypronyl(2,3,5-triiodobenzonate)

Methacrylic acid (6.0 g) was added to a cold stirred solution of 1,3-dicyclohexylcarbodiimide (14.2 g), 2-hydroxy(2,3,5-triiodobenzoyloxy)propyl methacrylate (45 g) and of 4-vinylpyrrilidinopyridine (1,1 g) in 200 ml of dichloromethane at such a rate that the resulting mixture was under gentle reflux (5 mins). The mixture was stirred overnight at room temperature then the precipitate was filtered off. The solid was washed with fresh dichloromethane and the combined organic solution was extracted with dilute HCl (2.0M), and then saturated sodium bicarbonate solution. Finally the organic phase was dried (MgSO$_4$). The solvent was removed under reduced pressure to give an almost colourless oil (41.2 g) which became semi-solid on standing.

Calc. for $C_{18}H_{17}O_6I_3$: C 30.45% found C=31.02%
H 2.39% found H=2.78%

The refractive index of this product was 1.600.

EXAMPLE 6

Preparation of bis[2,3,5-triiodobenzoyloxy) methacryloyloxypropyl]-benzene-1,2-dicarboxylate Solid 2,3,5-triiodobenzoic acid (28 g) was added to a cold stirred solution of 1,3-dicyclohexylcarbodiimide (11.5 g), bis(2-hydroxy-methacryloyloxypropyl)benzene-1,2-dicarboxylate [the reaction product of phthalic acid and glycidyl methacrylate] (16.0 g) and 4-pyrrolidinopyridine (0.8 g) in 200 ml of dichloromethane at such a rate that the stirred mixture was under gentle reflux (addition time 5 mins). The mixture was then stirred at room temperature for 24 hour. The solid that had separated was filtered off, washed with fresh dichloromethane and the combined organic phase extracted with dilute HCl (2.0M), saturated sodium bicarbonate solution and finally with dilute HCl. The organic phase was filtered through a column of silica and charcoal and then dried (MgSO$_4$) and the solvent removed under pressure to give the product (34.3 g) as a pale yellow oil.

Calc $C_{36}H_{28}O_{12}I_6$ C=30.58% found C=30.9%
H=1.98% found H=2.14%

The refractive index of the product was 1.607.

EXAMPLE 7

Preparation of 2-methacryloyloxyethyl(2,3,5-triiodobenzoate)

2,3,5-triiodobenzoic acid (25 g), 2-hydroxyethyl methacrylate (7.2 g), 1,3-dicyclohexylcarbodiimide (11.5 g) and 4-pyrrilidinopyridine (0.75 g) were stirred in ether suspension (250 ml) at room temperature for 24 hr. The solid was filtered off and the residue washed with fresh ether. The ether solution was extracted with dilute HCl (0.2M) and then with saturated sodium bicarbonate solution. The organic phase was dried (MgSO$_4$) and the solvent removed under reduced pressure. The residue (21.1 g) was recrystallised from ethyl acetate to give a pure material as white crystals m.pt.94° C.

Calc for $C_{13}H_{11}O_4I_3$ C=25.54% found C 25.38%
H=1.83% found H 1.88%

EXAMPLE 8

The following monomer mixtures A to K as detailed in Table 1, containing at least one of the monomers of Examples 1 to 7, were prepared by mixing the monomers with BisGMA or TEGDMA (triethyleneglycol dimethacrylate). The monomer mixtures A to K were suitable for use as the base resin compositions for the preparation of the dental compositions of the present invention.

TABLE 1

|   | BisGMA | TEGDMA | Ex 1  | Ex 2 | Ex 3 | Ex 4  | Ex 5 | Ex 6 | Ex 7 | Refractive Index |
|---|--------|--------|-------|------|------|-------|------|------|------|------------------|
| A |        |        | 50%   |      |      | 50%   |      |      |      | 1.632            |
| B |        |        |       |      |      |       | 50%  | 50%  |      | 1.616            |
| C |        | 9%     | 73%   |      |      |       |      |      | 18%  | 1.584            |
| D |        | 20%    |       |      | 10%  |       |      | 70%  |      | 1.578            |
| E |        | 20%    |       | 10%  |      |       |      | 70%  |      | 1.576            |
| F |        | 10%    |       |      |      |       | 45%  | 45%  |      | 1.573            |
| G |        | 24%    | 56%   |      |      |       |      |      | 20%  | 1.571            |
| H |        | 27%    | 63%   |      |      |       |      |      | 10%  | 1.567            |
| I |        | 30%    | 70%   |      |      |       |      |      |      | 1.564            |
| J | 35%    | 15%    | 44%   |      |      | 6%    |      |      |      | 1.560            |
| K |        | 25%    | 37.5% |      |      | 37.5% |      |      |      | 1.550            |

TEDGMA (tri-ethyleneglycol dimethacrylate)

TABLE 2

| | Filler | Refractive Index |
|---|---|---|
| L | quartz powder | 1.55 |
| M | powdered polymeric BisGMA | 1.5681 |
| N | wollastonite | 1.63 |
| O | hydroxyapatite | 1.64–1.65 |

The monomer mixture A to K as defined in Table 1 were incorporated into the dental compositions of the present invention choosing as the filler to match the Refractive Index of the monomer mixtures one of the fillers detailed in Table 2.

The following dental compositions in accordance with the present invention were prepared.

A. Quartz filler

Dental compositions were prepared from 50% by weight of silane treated quartz powder L (mean particle size 10 to 50 μm), 49% of one of the monomer mixtures C to K, 0.5% by weight of camphoroquinone and 0.5% by weight 2-(N, N-dimethylamino) ethyl methacrylate. The composition was curable using visible light.

B. Polymerized resin filler

Dental compositions were prepared from 50% by weight of a polymerized resin filler M (mean particle size 5 to 10 μm), 15% by weight of fumed silica (particle size 0.01 to 0.1 μm), 34% by weight of one of monomer mixtures C to K, 0.5% by weight camphoroquinone and 0.5% by weight 2-(N,N-dimethylamino)ethyl methacrylate. The composition was curable with visible light.

C. Wollastonite filler

Dental compositions were prepared from 60% by weight of silane treated wollastonite filler N (mean particle size 1 to 5 μm), 39% by weight of one of monomer mixtures A to C, 0.5% by weight camphoroquinone and 0.5% by weight 2-(N,N-dimethylamino) ethyl methacrylate. The composition was curable with visible light.

D. Hydroxyapatite filler

Dental compositions were prepared from 60% by weight of silane treated hydroxyapatite filler O (mean particle size 1 to 5 μm), 39% by weight of one of monomer mixtures A or B, 0.5% by weight camphoroquinone and 0.5% by weight 2-(N,N-dimethylamino) ethyl methacrylate. The composition was cured using visible light.

We claim:

1. A dental composition which comprises a resin base comprising at least one brominated or iodinated acrylate or methacrylate monomer having a high refractive index of above 1.6, in admixture with a filler material which has a refractive index of ±0.05 of the refractive index of the said resin base.

2. A dental composition as claimed in claim 1 wherein the iodinated acrylate or methacrylate monomer has the general formula:

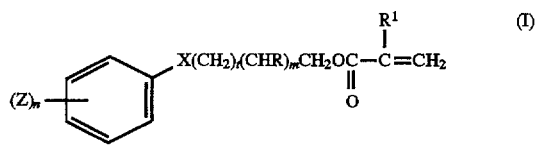

where X is selected from —O—

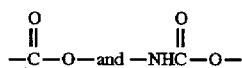

R is selected from H, OH, CH$_3$,

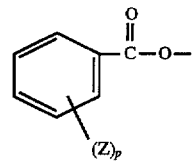

methacryloyloxy and acryloyloxy,

R$^1$ is selected from H and CH$_3$

Z is I m is selected from 0 and 1 n is 3 to 5 p is 3 to 5 and t is selected from 0 and 1, with the proviso that when X is O then R is selected from OH,

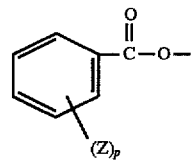

methacryloyloxy and acryloyloxy and m is 1.

3. A dental composition as claimed in claim 2 wherein the said monomer is selected from the group consisting of 2-(2,3,5-triiodobenzoyl)propylmethacrylate, 2-hydroxy-3-(2,4,6-triiodophenoxy)propylmethacrylate and 2-hydroxy-3-(2,3,5-triiodobenzoyloxy) propylmethacrylate.

4. A dental composition as claimed in claim 1 where the acrylate or methacrylate monomer has the general formula:

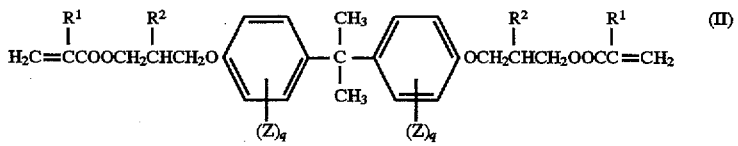

where $R^2$ is selected from H, OH and

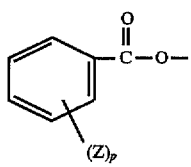

z is selected from Br, I, and a mixture of these substituents
p is 3 to 5
$R^1$ is selected from H and $CH_3$
q is 2 to 4 in each ring.

5. A dental composition as claimed in claim 1 wherein the iodinated monomer is 2,2(bis-[2-(2,3,5-triiodobenzoyloxy) 3-methacryloxypropoxy)phenyl)-propane.

6. A dental composition as claimed in claim 1 where the acrylate or methacrylate monomer has the general formula:

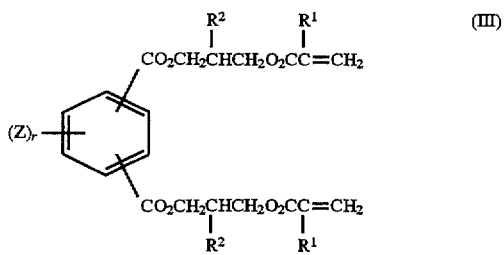

where $R^2$ is selected from H, OH and

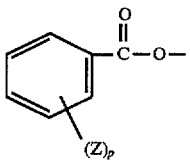

Z is selected from Br, I, and a mixture of these substituents

P is 3 to 5

$R^1$ is selected from H and $CH_3$ r is 1 to 4.

7. A dental composition as claimed in claim 1 where the iodinated monomer is bis[2-(2,3,5-triiodobenzyloxy) methacryloyloxypropy]-benzene-1,2-dicarboxylate.

8. A dental composition as claimed in claim 1 wherein the filler material is radio-opaque.

9. A dental composition as claimed in claim 1 wherein the filler material is apatite, hydroxyapatite, a modified hydroxyapatite, wollastonite or a powdered cross-linked polymer.

10. A dental composition as claimed in claim 9 wherein the filler material has a particle size in the range of from 0.5 to 50µm.

11. A dental composition as claimed in claim 1 wherein the resin base additionally comprises at least one additional component selected from the group consisting of an acrylate monomer, a methacrylate monomer, an acrylate polymer and a methacrylate polymer.

12. A dental composition as claimed in claim 1 wherein the resin base includes a curing system which comprises a free radical catalyst or a photoinitiator.

13. A dental composition as claimed in claim 1 wherein the curing system comprises a peroxide/amine initiator system, or a camphoroquinone/tertiary amine system.

14. A dental composition as claimed in claim 1 wherein the filler material has a refractive index of within ±0.005 of the base resin.

* * * * *